United States Patent [19]

Niina et al.

[11] Patent Number: 4,671,941
[45] Date of Patent: Jun. 9, 1987

[54] POLYNUCLEOTIDE SYNTHESIZING APPARATUS

[75] Inventors: Akihiko Niina, Yokohama; Tatsuo Ohira, Tokyo; Shigemi Miyamoto, Yokohama, all of Japan

[73] Assignee: Nippon Zeon Co. Ltd., Tokyo, Japan

[21] Appl. No.: 670,939

[22] Filed: Nov. 13, 1984

[30] Foreign Application Priority Data

Nov. 14, 1983 [JP] Japan .................. 58-213616

[51] Int. Cl.$^4$ .......................... B01J 8/02; C07K 1/00; C12N 15/00
[52] U.S. Cl. .................... 422/131; 422/116; 422/188; 435/287; 935/88
[58] Field of Search ............... 422/116, 131, 134, 103, 422/188, 196; 435/91, 312, 317, 287; 935/88; 525/54.11

[56] References Cited

U.S. PATENT DOCUMENTS

| 3,531,258 | 9/1970 | Merrifield et al. | 422/116 |
| 3,647,390 | 3/1972 | Kubodera et al. | 422/116 |
| 4,153,416 | 5/1979 | Bonner et al. | 422/67 X |
| 4,362,699 | 12/1982 | Verlander et al. | 422/131 |
| 4,517,338 | 5/1985 | Urdea et al. | 422/116 |

Primary Examiner—S. Leon Bashore
Assistant Examiner—Andrew J. Anderson
Attorney, Agent, or Firm—Shlesinger Arkwright Garvey & Fado

[57] ABSTRACT

In an apparatus for synthesizing polynucleotide including a plurality of reactors, bottles charged with reagents and solvents, and change valve means for switching passages between respective bottles and the reactors, the improvement comprises mode selector means between a pressure source and the reactors for switching liquid supply or discharge operation and distributor means for closing or opening passages connected with the reactors to selectively operate the reactors.

8 Claims, 12 Drawing Figures

POLYNUCLEOTIDE SYNTHESIZING APPARATUS

BACKGROUND OF THE INVENTION

The present invention relates to an apparatus for synthesizing polynucleotides.

A well-known method of synthesizing polynucleotides, for example DNA (deoxyribonucleic acid) is such that a support chemically combined with nucleotide is used, and nucleotide is sequentially condensed by phosphotriester method, phosphodiester method, phosphite method and the like.

This synthesizing process includes the steps of washing, deprotection, washing, condensation reaction, washing, coupling and repeating the afore-mentioned steps. The types of steps are not many. However, many tedious repetitive operations are required.

The present inventors have proposed a polynucleotide synthesizing apparatus in Japanese Patent Application No. 58-161637 for eliminating the tediousness of the synthesis operation.

The proposed polynucleotide synthesizing apparatus comprises an apparatus body which is equipped with two reactors, a plurality of containers which are charged with reagents and solvents and the like necessary for polynucleotide synthesis reaction and a change valve for changing the passages between the containers and the reactors by operating a knob and liquid supplying means for feeding the reagents and solvents and the like from the respective containers to the reactors under the pressure of an inert gas.

This synthesizing apparatus can eliminate the tediousness of the synthesis operation. By operating a three-way valve along the passage between a top inlet of the reactor and the change valve, liquid can be simultaneously supplied to two reactors or alternatively liquid may be supplied to only one reactor.

However there is a problem in which liquid supply and discharge to and from one reactor can not be repeated while the other reactor is charged with the solvent and reagent, or reaction can not be continued in one reactor while reaction is stopped or terminated in the other reactor.

SUMMARY OF THE INVENTION

It is therefore an object of the present invention to provide a novel apparatus for synthesizing polynucleotide.

It is another object of the present invention to provide an apparatus for synthesizing polynucleotide.

It is another object of the present invention to provide an apparatus for synthesizing polynucleotide in which a reaction can be performed in one reactor independently of the other reactor.

It is a further object of the present invention to provide a polynucleotide synthesizing apparatus including a plurality of reactors in which a reaction can be continued in one reactor while reactions are stopped or terminated in the other reactors.

In accordance with the present invention, there is provided an apparatus for synthesizing polynucleotides which includes a plurality of reactors, bottles which are charged with reagents and solvents, and change valve means for switching passages between respective bottles and the reactors, the improvement comprising mode selector means between a pressure source and the reactors for switching liquid supply or discharge operation and distributor means for closing or opening passages connected with the reactors to selectively operate the reactors.

The mode selector means preferably includes mode selector valves, each corresponding to respective reactors.

The mode selector valves preferably form an integrated valve in which the mode selector valves are operatively connected with each other.

Each mode selector valve is preferably a four-way change valve.

The mode selector valve preferably includes a first port connected with the pressure source, second and third ports connected with top and bottom ports of the reactor respectively and a fourth port connected with a drain.

The first and second ports are preferably communicated with the third and fourth ports respectively when the mode selector valve is at the feed position and the first and third ports are communicated with the second and fourth ports respectively when the valve is at the blow position.

The distributor means includes a first distribution valve connected between the change valve means and the reactors and a second distributor valve between the pressure source and the mode selector means.

The first and second distribution valves preferably include first and second three-way valves respectively.

The first and second distributor valves are preferably operatively connected with each other.

The first distributor valve preferably has a port connected with the change valve means and a plurality of ports, each connected with respective reactors.

The first distributor valve further includes a port connected with a vacuum source.

The second distributor valve preferably includes one port connected with the pressure source and a plurality of ports, each connected with mode selector means.

BRIEF DESCRIPTION OF THE DRAWINGS

FIG. 2b is a sectional view along line A—A of FIG. 2a;

FIG. 2c is a sectional view along line B—B of FIG. 2a;

FIG. 5b is a sectional view along the line C—C of FIG. 5a;

FIG. 5c is a sectional view along the line D—D of FIG. 5a;

DETAILED DESCRIPTION OF THE EMBODIMENTS

Figure 1:
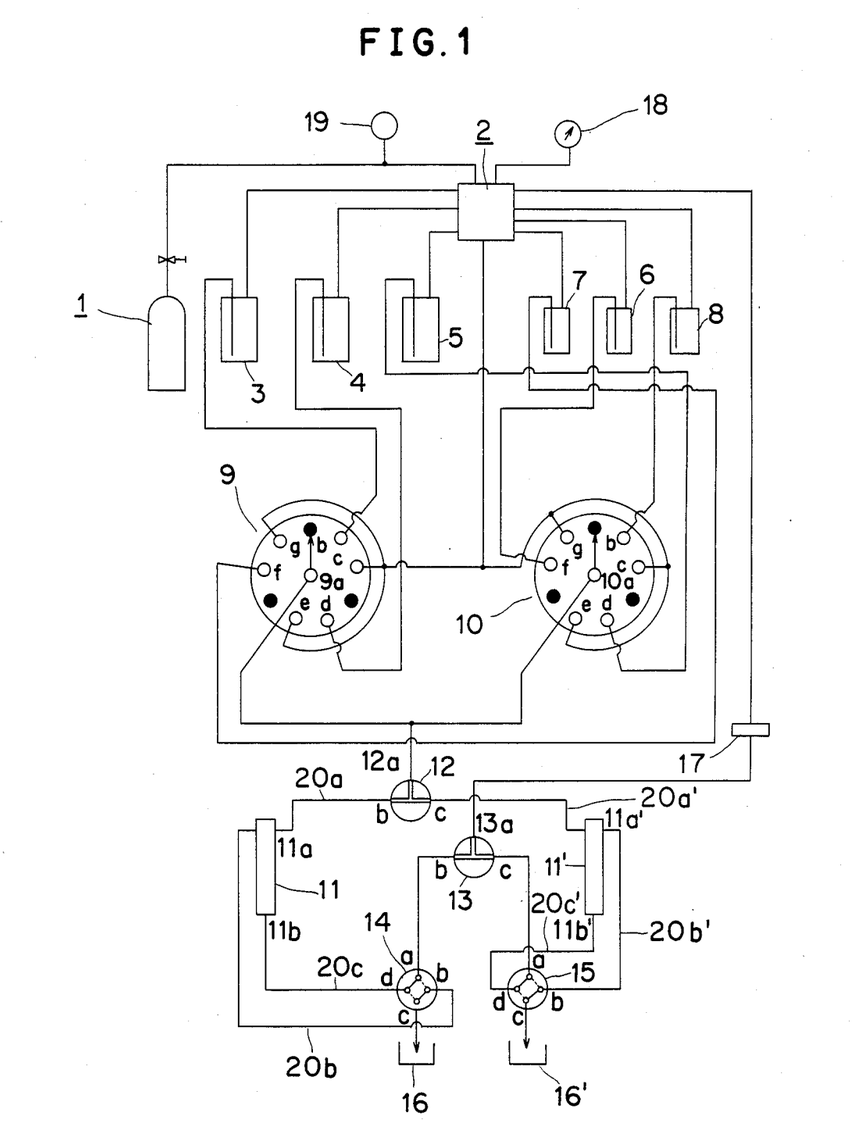
FIG. 1 is a schematic diagram showing a first embodiment of the apparatus of the present invention.

The outline of the entire synthesizing apparatus of the present invention will be described with reference to FIG. 1. In the drawings reference numeral 1 represents a nitrogen cylinder, 2 a distributor, 3 to 6 bottles, 7 and 8 reservoirs, 9 and 10 change valves, 11 and 11' reactors, 12 and 13 three-way valves (distributors), 14 and 15 four-way valves (mode selectors), 16 and 16' waste-liquid reservoirs, 17 a line filter, 18 a pressure gauge, 19 a safety valve.

The bottles 3, 4 and 5 are charged with solvent I, detrythyl agent/solvent I solution and solvent II respectively. The bottle 6 is charged with deactivation agent and deactivation auxiliary agent. The reservoirs 7 and 8 are charged with solvents suitable for the particular kind of detrythyl agent in use and are used when the detrythyl agent is changed.

The change valves 9 and 10 serve to change the passages between the bottles 3 to 6, reservoirs 7 and 8 and the reactors 11 and 11'. The change valve 9 includes a common port 9a which communicates with the reactors 11 and 11' via the three-way valve 12, change ports 9b, 9d and 9f for reagent and solvent which communicate with the bottles 3 and 4 and the reservoir 7 respectively, and change ports 9c, 9e and 9g for gas which communicate with the distributor 2.

The change valve 10 includes a common port 10a which communicates with the reactors 11 and 11' via the three-way valve 12, change ports 10b, 10d and 10f for reagent and solvent which communicate with the reservoir 8 and the bottles 5 and 6, and the change ports 10c, 10e and 10g for gas which communicate with the distributor 2.

The nitrogen gas in the nitrogen cylinder 1 is fed to the distributor 2 where the gas is distributed to the bottles 3 to 6 and the reservoirs 7 and 8.

By switching the ports 9b to 9g and the ports 10b to 10g of the change valves 9 and 10 respectively, solvents and reagents and the like are fed to the reactors 11 and 11' via the three-way valve 12 and the passages 20a and 20a' from the bottles 3 to 6 and the reservoirs 7 and 8 by the pressure of $N_2$ gas. $N_2$ gas is also fed to the reactors 11 and 11' from the distributor 2 via the three-way valve 12 and the passage 20a.

When the solvents and the reagents are to be fed to the reactors the four-way valves 14 and 15 are brought into a position (FEED) represented by a solid line. This causes pressure purge from the top port of the reactors 11 and 11' via the passages 20b and 20b', and the four-way valves 14 and 15. Simultaneously with this, $N_2$ gas having an amount required for bubbling is blown from the bottom port of the reactors 11 and 11' via the distributor 2, the line filter 17, the three-way valve 13, the four-way valves 14 and 15 and the passages 20c and 20c'.

When the solvent etc. is to be discharged from the reactors 11 and 11', the four-way valves 14 and 15 are brought into a position (BLOW) represented by a dotted line. This causes the solvent to discharge from bottom port to the waste liquid reservoirs 16 and 16' via the passages 20c and 20c' and the four-way valves 14 and 15.

The ports 9b to 9g and 10b to 10g of the change valves 9 and 10 are disposed in the order of liquid supply and discharge sequence. The liquid supply and discharge sequence in one condensation step is completed by firstly switching the ports 9b to 9g and then the ports 10b to 10g. A different port sequence may be used, however.

The line filter 17 has a function to adjust the flow rate of $N_2$ gas into an amount necessary for the bubbling as well as a function to remove the contaminants.

When DNA is to be synthesized, the reactors 11 and 11' are charged with support chemicals which are combined with nucleotides and wetted with solvent I.

Thereafter detrythylation, washing of the reactors with solvent I and washing of the reactors with solvent II are subsequently carried out. At this time the reactors are heated by means of the heater 39 (refer to FIG. 6) and bubbling is carried out by $N_2$ gas. After completion of the condensation reaction the liquid is discharged from the reactors 11 and 11'. After the reactors are washed with solvent II, the capping reaction is carried out. Then the reactors are washed with solvent I.

By repeating this operation the nucleotide chains are successively elongated.

The essential part of the present invention will be described. The afore-mentioned three-way valve 12 is provided along the passages 20a, 20a' between one inlet or outlet port 11a, 11a' of the reactors 11, 11' and the change valves 9 and 10 and serves to open and close the passages 20a, 20a'. The three-way valve 13 is provided along the passages 20c, 20c' which communicate with the other port 11b, 11b' of the reactors 11 and 11' and serves to open and close the passages 20c and 20c'.

Figure 2A:
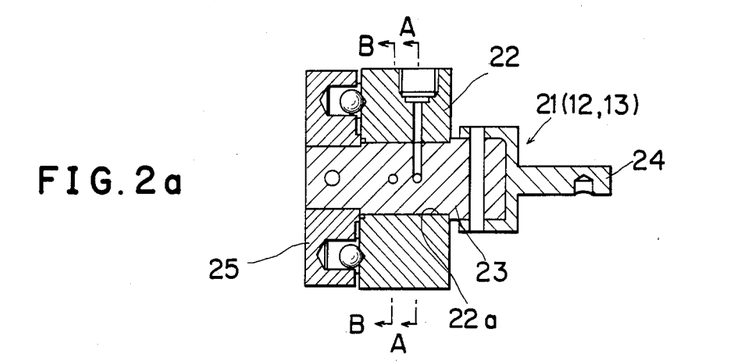
FIG. 2a is a sectional view showing a dual three-way valve.
Figure 2B:
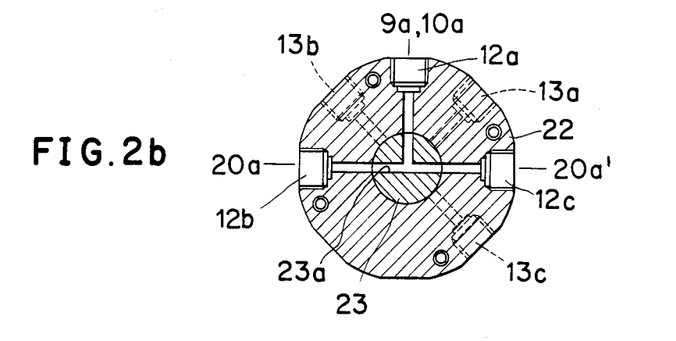
Figure 2C:
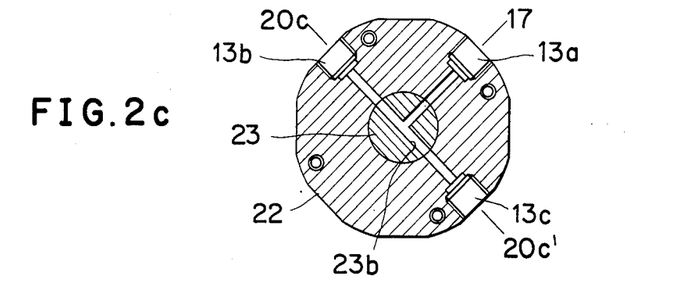

The three-way valves 12 and 13 are integrally formed as a dual three-way valve 21 as shown in FIGS. 2a to 2c. The dual three-way valve 21 comprises a cock body 22 made of synthetic resin such as a fluorine compound and metal and a cock plug 23 made of synthetic resin such as fluorine compound.

The cock body 22 is provided with the ports 12a to 12c of the three-way valve 12 and the ports 13a to 13c of three-way valve 13. The ports 12a to 12c and 13a to 13c are positioned at different positions along the axis of the cock body 22 and are positioned at different angular positions around the axis thereof as shown in FIG. 2a. The port 12a communicates with the common ports 9a and 10a of the change valves 9 and 10. The port 12b communicates with the passage 20a. The port 12c communicates with the passage 20a'. The port 13a communicates with the line filter 17. The ports 13b and 13c communicate with the passages 20c and 20c' respectively.

The cock plug 23 is provided with a T-shaped passage 23a which connects or disconnects the ports 12a to 12c with each other, and a T-shaped passage 23b which connects or disconnects the ports 13a to 13c with each other.

The cock plug 23 is rotatably inserted into the central bore 22a of the cock body 22. The cock plug 23 is provided with a operation knob 24 at one end thereof projecting beyond the bore 22a and is provided with a click mechanism 25 for positioning the cock plug 23 at given angular positions at the other end thereof.

When the ports 12a to 12c communicates with each other and the ports 13a to 13c communicate with each other (FIG. 1 and FIGS. 2a to 2c), the solvents and the like are simultaneously supplied to the reactors 11 and 11' via the three-way valve 12 while $N_2$ gas for bubbling is simultaneously blown into the reactors 11 and 11' via the line filter 17 and three-way valve 13.

When the cock plug 23 is clockwise rotated by 90° from the angular position shown in FIGS. 2b and 2c by the operation of the knob 24, the port 12a is brought into communication with the port 12c and out of communication with the port 12b, and the port 13a is brought into communication with port 13c and out of communication with the port 13b. As the result of this, solvents and the like may be supplied to or charged in one reactor 11 or 11' while the solvent and the like are not charged in the other reactor 11 or 11'. Similarly, one reactor 11 or 11' may be used.

When solvent is to be discharged, for example from reactor 11', the four-way valve 15 is positioned at a position BLOW (represented by a dotted line). The four-way valve 14 is also positioned at a position BLOW since the four-way valve 15 and 14 forms an integral dual four-way valve 26 (refer to FIGS. 5a to 5c). When the four-way valve 14 is positioned at the position BLOW, the port 11b' of the other reactor 11' is brought into communication with waste liquid reservoir 16'. $N_2$ gas from the line filter 17 is now blown into the top space of the reactor 11'. There is no fear that the solvent and the like discharged since the liquid level within the reactor 11' is slightly lowered so that the top space is evacuated to balance with the pressure in the passage 20c'. At this time, $N_2$ gas is blown into the top space of the reactor 11' via the three-way valve 13, four-way valve 15 and the passage 20b' so that the solvents and the like are discharged under the pressure of the $N_2$ gas.

If the passage 20c' is blocked for some reason while the solvents and the like are discharged from reactor 11', the solvents and the like overflow to the passage 20b' from the reactor 11'. There is no fear that they flow into the other reactor 11 since the port 13c is not connected with the port 13b.

Conventional apparatus is not provided with means equivalent to the three-way valve 13 so that such apparatus has a problem in which solvents and the like flow from one reactor to the other reactor to hinder the reaction in the other reactor. This problem may be solved by the present invention.

Figure 3:
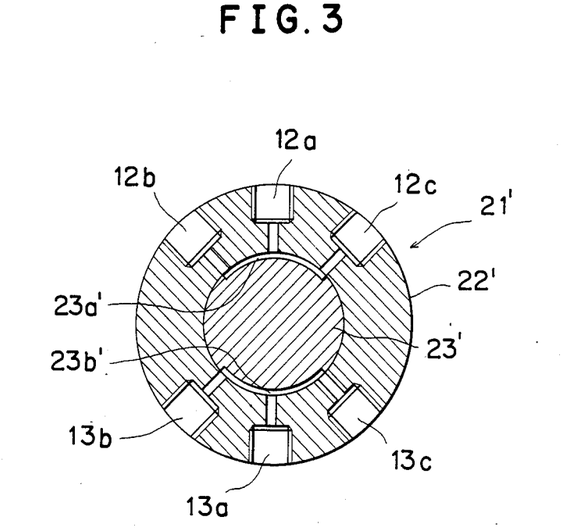
FIGS. 3 and 4 are sectional views showing other embodiments of the dual three-way valve.
Figure 4:
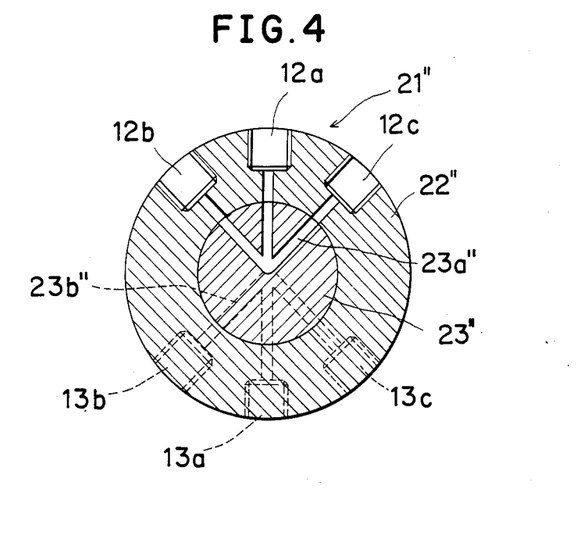

FIGS. 3 and 4 show other embodiments of dual three-way valves 21' and 21".

The dual three-way valve 21' shown in FIG. 3 includes the ports 12a to 12c and 13a to 13c which are positioned at the same position along the axis of the cock body 22'. Peripheral recesses 23a' and 23b' are formed on the outer periphery of the cock plug 23' for communication among the ports 12a to 12c and the ports 13a to 13c respectively.

Figure 5A:
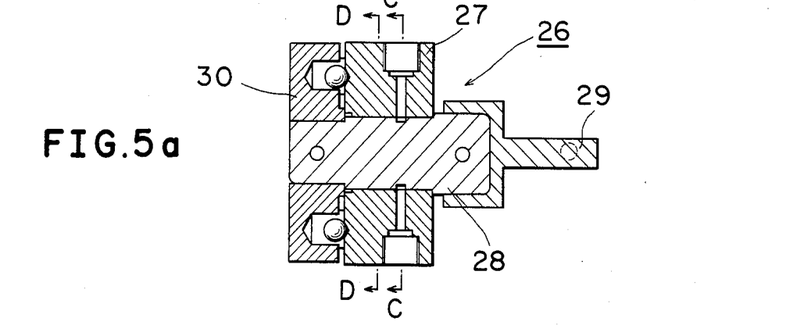
FIG. 5a is a sectional view showing a dual four-way valve.
Figure 5B:
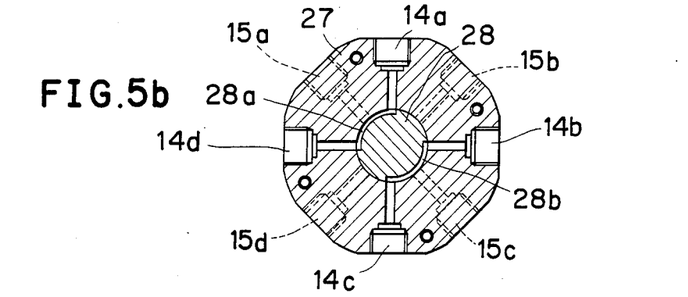
Figure 5C:
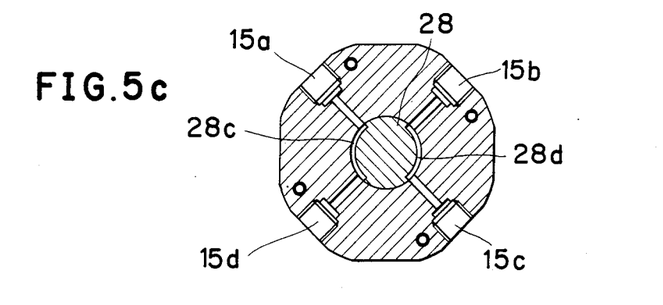

The dual three-way valve 21" shown in FIG. 4 includes the ports 12a to 12c and the ports 13a to 13c which are positioned at different positions along the axis of the body 22" and are symmetric around the axis. The cock plug 23" is formed with substantially three-forked passages 23a" and 23b" for connecting or disconnecting the ports 12a to 12c and the ports 13a to 13c respectively. FIG. 5a to 5c show the structure of a afore-mentioned dual four-way valve 26 in detail. A cock body 27 and a cock plug 28 are formed of a material identical with that of the dual three-way valve.

The cock body 27 is formed with the ports 14a to 14d of the four-way valve 14 and the ports 15a to 15d of the four-way valve 15. The ports 14a to 14d and the ports 15a to 15d are positioned at different positions along the axis of the body 27 and positioned at angularly different positions by 45° as shown in FIG. 5b. Peripheral grooves 28a to 28d are formed on the outer periphery of the cock plug 28.

The ports 14a and 14b communicate with the ports 14d and 14c via the peripheral grooves 28a and 28b, respectively at position FEED. The ports 15a and 15b also communicate with the ports 15d and 15c respectively in a similar manner at this position. The ports 14a and 14c communicate with the ports 14b and 14d via the grooves 28a and 28b at the BLOW position respectively when the cock plug 28 is rotated 90°. Also, at this position the ports 15a and 15c communicate with the ports 15b and 15d via the peripheral grooves 28c and 28d respectively.

An operation knob 29 is provided at one end of the cock plug 28 and a click mechanism 30 is provided at the other end for positioning the cock plug at predetermined angular positions.

Figure 6:
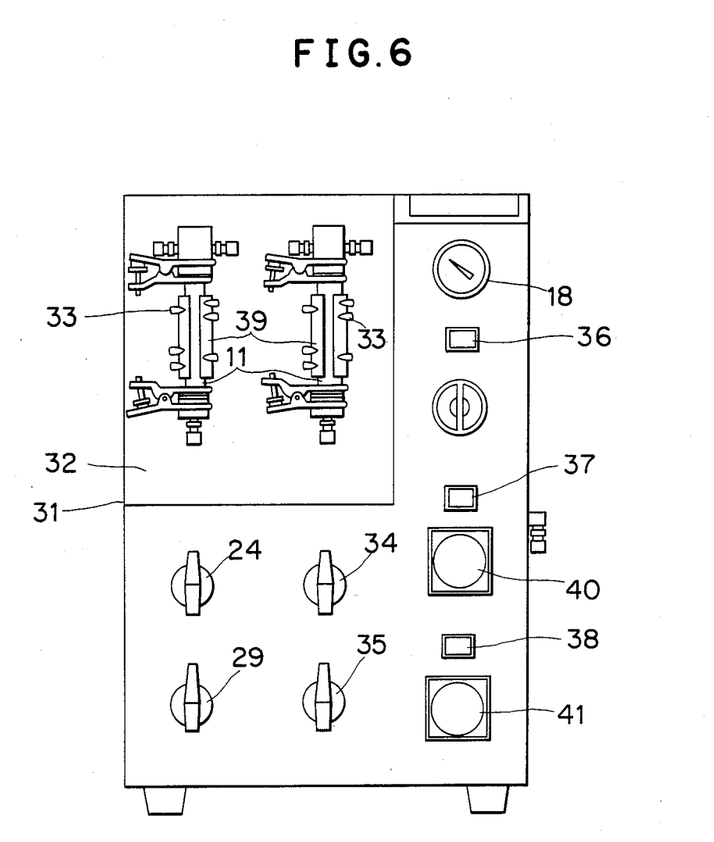
FIG. 6 is a front view showing the appearance of the apparatus.

FIG. 6 shows the appearance of the synthesizing apparatus. An attachment portion 32 is formed on the front panel of a casing 31. The attachment portion 32 is a recess which opens at the side and the upper faces of the casing 31. The reactors 11 and 11' are mounted on the attachment portion 32 by means of support members 33. The operation readiness of the reactors 11 and 11' is excellent since the attachment portion 32 opens at side and upper faces as well as the front face. A transparent or semitransparent cover is attached to the attachment portion 32 when the apparatus is not used.

The pressure gauge 18, the knob 24 for three-way valves 12 and 13 and the knob 29 for the four-way valves 14 and 15 are disposed on the front panel of the casing 31. Knobs 34 and 35 for the change valves 9 and 10, lighting switches 36, 37 and 38, knobs for adjusting the temperature of the heater 39 are also disposed on the front panel.

Figure 7:
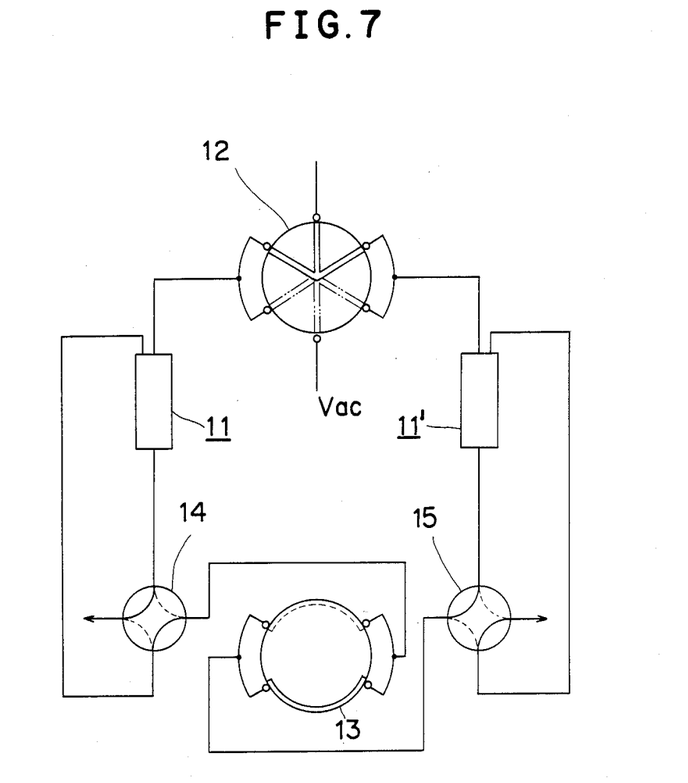
FIGS. 7 and 8 are schematic diagrams showing second and third embodiments of the essential parts of the present invention respectively.

FIG. 7 shows a second embodiment of the present invention in which the reactors 11 and 11' are connected with a vacuum pump Vac so that simultaneous boiling and dehydration can be accomplished when the three-way valve 12 is switched to a position represented by the dotted line. Suction can be applied to the top of the reactors 11 and 11' if three-way valve 13 is arranged to connect with the vacuum pump Vac.

Figure 8:
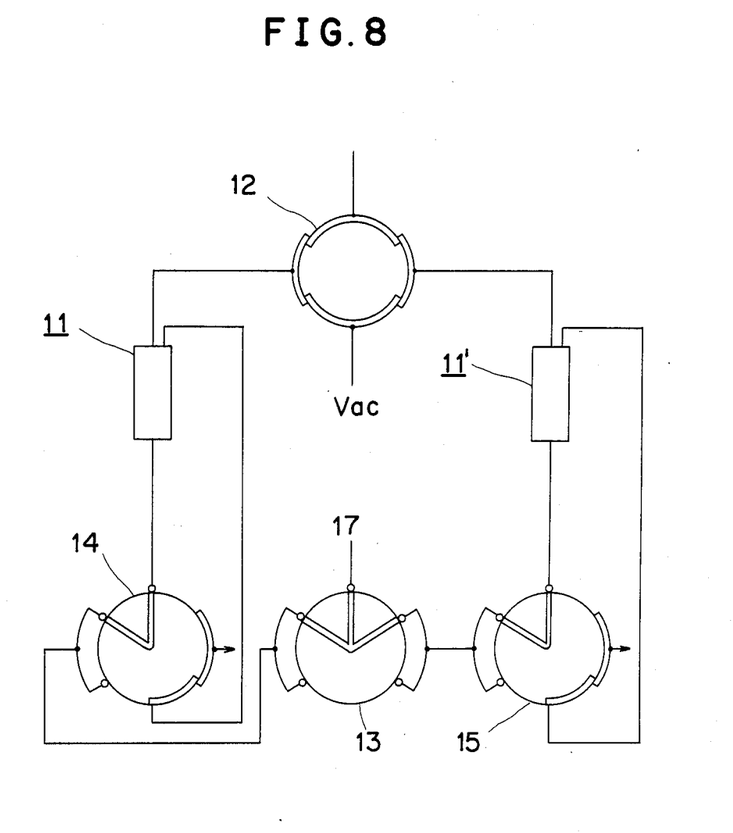

FIG. 8 shows a third embodiment of the present invention in which simultaneous boiling and dehydration can be accomplished when the reactors 11 and 11' are connected with the vacuum pump Vac.

In this embodiment, the three-way valves 12 and 13 which are distributors form an integrated dual three-way valve 21. The valves 12 and 13 are operatively switched. However the present invention is not limited to such a structure. For example the valves 12 and 13 may be independently switched. In brief, the valves 12 and 13 can close or open the passages 20a and 20c connected with the ports 11a and 11b respectively for switching the reactors 11 and 11'. In the disclosed embodiment only one knob 24 is needed and one operation enables both three-way valves 12 and 13 to be switched so that the operation is easy. Although two reactors are shown, more than two reactors may be used.

The synthesizing apparatus in which $N_2$ gas is used as a liquid supplying means and the passages are switched by means of two change valves 9 and 10 has been described in the afore-mentioned embodiments. The present invention is not limited to such an arrangement. A liquid supply pump may be used as liquid supplying means and a valve is provided for each passage for switching the passage.

In other words, the present invention is broadly applicable to a synthesizing apparatus which includes an apparatus body equipped with reactors, reagent and solvent bottles which are charged with reagents and solvents which are necessary for polynucleotide synthetic reactions and switch means for switching the passages communicating between the reagent and solvent bottles and the reactors, whereby the reagents and solvent and the like are subsequently supplied to the reactors from the bottles.

In accordance with the present invention, a plurality of reactors are provided. A mode selector (dual four-way valve) for switching the liquid supply or discharge operation is provided at one port of the reactor and a distributor (three-way valves 12, 13 and dual three-way valve 21) is provided for opening and closing the passages for selectively operating the reactors at a passage connected with one port of the reactors and a passage connected with the other port of the reactors. Various reaction modes are therefore accomplished. For example reaction is simultaneously carried out in all reactors. Alternatively reaction is carried out in one reactor. Alternatively reaction is continued in one reactor while the reaction is stopped or terminated in the other reactor. It is convenient to use the apparatus.

Accordingly the efficiency of the synthesizing operation may be enhanced. There is no fear that the solvents and the like in one reactor will enter the other reactors.

What is claimed is:

1. An apparatus for synthesizing polynucleotides including two reactors, bottles charged with reagents and solvents, and change valve means for switching passages between the respective bottles and the reactors, the improvement comprising:
   (a) mode selector means between a pressure source and the reactors for switching between liquid supply and discharge operations, said mode selector means including a mode selector valve operatively connected to each reactor, each said mode selector valve comprising a four-way change valve; and,
   (b) distributor means for closing and opening the passages connected with the reactors to operate the reactors selectively, said distributor means including a first three-way valve connected between the change valve means and the reactors and a second three-way valve connected between the pressure source and the mode selector means.

2. The apparatus as defined in claim 1, in which the mode selector valves form an integrated valve in which the mode selector valves are operatively connected with each other.

3. The apparatus as defined in claim 1, in which each mode selector valve includes a first port connected with the pressure source, second and third ports connected with top and bottom ports of the reactor to which the mode selector valve corresponds, and a fourth port connected with a drain.

4. The apparatus as defined in claim 3, in which the first and second ports communicate with the third and fourth ports respectively when the mode selector valve is at a position for feeding reagents and solvents into the reactor corresponding to the valve, and the first and third ports communicate with the second and fourth ports respectively when the mode selector valve is at a position for discharging liquid from the reactor corresponding to the valve.

5. The apparatus as defined in claim 1, in which the first and second three-way valves are operatively connected with each other.

6. The apparatus as defined in claim 1, in which the first three-way valve has a port connected with the change valve means and a plurality of ports each connected with a respective reactor.

7. The apparatus as defined in claim 6, in which the first three-way valve further includes a port connected with a vacuum source.

8. The apparatus as defined in claim 1, in which the second three-way valve includes one port connected with the pressure source and a plurality of ports each connected with the mode selector means.

* * * * *